United States Patent [19]

Augustine et al.

[11] Patent Number: 5,300,102

[45] Date of Patent: * Apr. 5, 1994

[54] THERMAL BLANKET

[75] Inventors: Scott D. Augustine, Bloomington; Randall C. Arnold, Maplewood, both of Minn.

[73] Assignee: Augustine Medical, Inc., Eden Prairie, Minn.

[*] Notice: The portion of the term of this patent subsequent to Feb. 9, 2010 has been disclaimed.

[21] Appl. No.: 887,233

[22] Filed: May 19, 1992

Related U.S. Application Data

[63] Continuation of Ser. No. 550,757, Jul. 10, 1990, abandoned, which is a continuation-in-part of Ser. No. 227,189, Aug. 2, 1988, abandoned, which is a continuation-in-part of Ser. No. 104,682, Oct. 5, 1987, abandoned.

[51] Int. Cl.$^5$ .............................................. A61F 7/00
[52] U.S. Cl. ..................................... 607/107; 165/46; 5/482
[58] Field of Search ................. 128/400, 380, 367–369, 128/373, 403, 379; 5/423, 482; 165/46; 34/98, 99; 219/12; 4/535–537

[56] References Cited

U.S. PATENT DOCUMENTS

| | | | |
|---|---|---|---|
| 2,110,022 | 3/1938 | Kliesrath | 5/423 |
| 3,243,827 | 4/1966 | Kintner | 5/482 |
| 3,714,947 | 2/1973 | Hardy | 128/400 |
| 4,572,188 | 2/1986 | Augustine et al. | 128/380 |
| 4,660,388 | 4/1987 | Greene, Jr. | 4/585 |

Primary Examiner—Mark S. Graham
Attorney, Agent, or Firm—Baker, Maxham, Jester & Meador

[57] ABSTRACT

A thermal blanket includes an inflatable covering with a head end, a foot end, two edges and an undersurface. The covering is inflated through an inlet at the foot end by a thermally-controlled inflating medium. An aperture array on the undersurface of the covering exhausts the thermally controlled inflating medium from the covering. Exhaust port openings are provided at the edges of the covering to vent the inflating medium, which enhances circulation of the thermally-controlled medium through the cover. An uninflatable section is provided at the head end, together with an absorbent bib attached to the covering, adjacent the uninflatable section. An uninflatable section may also be provided at the foot end having a pair of seams to form an erectable drape section. The enhanced circulation of the medium through the covers maintains a relatively high average temperature under the blanket and a relatively uniform distribution of temperature in the inflating medium which is exhausted through the apertures into the structure's interior. When the structure covers a patient, the uninflatable section at the head end provides a relatively unobstructed view of the patient's face, while the absorbent bib maintains a relatively sanitary environment in the area beneath the patient's head. The uninflatable section at the foot end retains heat from the inflating medium to warm the patient's feet and insulate the bare skin of the feet from excessive conductive heat from the hose connected to the inflation inlet.

18 Claims, 3 Drawing Sheets

THERMAL BLANKET

RELATED APPLICATIONS

This is a continuation of application Ser. No. 07/550,757 filed Jul. 10, 1990, abandoned, which is continuation-in-part of application Ser. No. 07/227,189, abandoned filed Aug. 2, 1988, which is a continuation-in-part of application Ser. No. 07/104,682, abandoned filed Oct. 5, 1987.

BACKGROUND OF THE INVENTION

This invention relates to thermal blankets used in a medical setting to deliver a bath of a thermally-controlled medium to a patient.

The thermal blanket prior art is best expressed in our prior U.S. Pat. No. 4,572,188 entitled "AIRFLOW COVER FOR CONTROLLING BODY TEMPERATURE." In our prior patent, a self-erecting, inflatable airflow cover is inflated by the introduction into the cover of a thermally-controlled inflating medium, such as warmed air. When inflated, the cover self-erects about a patient, thereby creating an ambient environment about the patient, the thermal characteristics of which are determined by the temperature of the inflating medium. Holes on the underside of our prior art airflow cover exhaust the thermally-controlled, inflating medium from inside the cover to the interior of the erected structure. Our airflow cover is intended for the treatment of hypothermia, as might occur postoperatively.

Evaluation of our airflow cover by skilled practitioners has resulted in general approbation: the opinion is that the airflow cover efficiently and effectively accomplishes its purpose of giving a thermally-controlled bath. We have realized, however, that, while our prior art airflow cover achieves its objective, certain improvements to it are necessary in order to realize additional clinical objectives and to enjoy further advantages in its use.

SUMMARY OF THE INVENTION

We have improved the clinical usefulness of our self-erecting airflow cover by observing that controlling the contour of its inflatable portion at its head end to define a generally concave non-inflatable portion will permit a care giver to more easily observe a patent's head, face, neck and chest. Further, we have observed that limited venting of the thermally controlled inflating medium from the edges of the cover results in more efficient, more uniform heating within the cover. We have also observed that it is good clinical practice to keep the area of the care site in the vicinity of the patient's head and face as clean as possible. Still further, we have observed that modification of the foot end of the self-erecting airflow cover to define a non-inflatable but erectable drape section retains heat from the inflating medium to warm the patient's feet and insulate the bare skin of the feet from excessive heat from the inlet hose.

These four observations have resulted in an improved thermal blanket in which a self-erecting inflatable covering has a head end, a foot end, two edges, and an undersurface. An inflating inlet adjacent said foot end admits a thermally-controlled inflating medium into the covering. An aperture array on the undersurface of the covering exhausts the thermally-controlled inflating medium from the covering into the structure created when the covering self-erects upon inflation. The improvements to this basic structural complement include an uninflatable section at the head end of the covering, exhaust port openings at the edges of the covering, an absorbent bib attached to the covering at the head end adjacent the uninflatable section, an uninflatable electable drape section at the foot end of the covering and structural features that make the covering simple and economical to produce.

With these improvements, the thermal blanket, when inflated and erected over a patient, delivers the thermally-controlled inflating medium into the interior of the structure covering the patient, thereby thermally bathing the patient. The first improvement permits full viewing of the head and face of the patient from almost any aspect around the thermal blanket. The exhaust port openings increase the rate of circulation of the inflating medium within the blanket, thereby increasing the temperature within the structure and making the temperature distribution more uniform. The absorbent bib soaks up and retains liquids which might otherwise spread over the care sit in the area of a patient's head. Such liquids can include the patient's own perspiration, blood, vomit, saliva, or liquids which are administered to the patient. The absorbent bib also acts to some extent to seal the head end of the inflated structure. The non-inflatable erectable drape section at the footend of the covering retains heat around the patient's feet and insulates the bare skin of the feet.

From another aspect, the invention is a thermal blanket for covering and bathing a person in a thermally-controlled medium. The thermal blanket includes a flexible base sheet having a head end, a foot end, two edges, and a plurality of apertures opening between the first and second surface of the base sheet. An overlying material sheet is attached to the first surface of the base sheet by a plurality of discontinuous seams which form the material sheet into a plurality of substantially parallel, inflatable chambers. A continuous seam is provided between the material sheet and the base sheet at the head end to form a non-inflatable viewing recess at the head end. Exhaust port openings are provided through the material sheet to vent the medium from the chambers away from the base sheet. An absorbent bib is attached to the head end in the vicinity of the viewing recess. A continuous seam is provided between the material sheet and the base sheet at the foot end to form a non-inflatable, erectable drape section to cover the patient's feet.

Therefore the invention accomplishes the important objective of providing a self-erecting, inflatable thermal blanket that permits a relatively unobstructed view of a patient's head and face when in use.

Another objective is the efficient and uniform heating of the interior of the structure created when the blanket is inflated with a heat inflating medium.

Another objective is providing a covering for a patient's feet that helps retain the heat inflating medium around the patient.

A further objective of the invention is the provision of such a blanket with a means for maintaining the cleanliness of the care site in the vicinity of the patient's head and face.

The advantageous simplified structure of the thermal blanket make its production straight forward and economical.

These and other important objectives and advantages will become evident when the detailed description of the invention is read with reference to the below-summarized drawings, in which.

DETAILED DESCRIPTION OF THE PREFERRED EMBODIMENTS

When used herein, the term "thermal blanket" is intended to be interchangeable with, but not necessarily limited by, the term "airflow cover" used in our U.S. Pat. No. 4,572,188, which is incorporated herein in its entirety by reference. In this description, the term "thermal blanket" is meant to invoke a self-erecting, inflatable structure for delivering a thermally-controlled inflating medium to the interior of the structure created when the thermal blanket is inflated. The purpose of the thermal blanket is to efficiently administer a uniformly thermally-controlled bath of the inflating medium to a patient within the erected structure.

Figure 1:
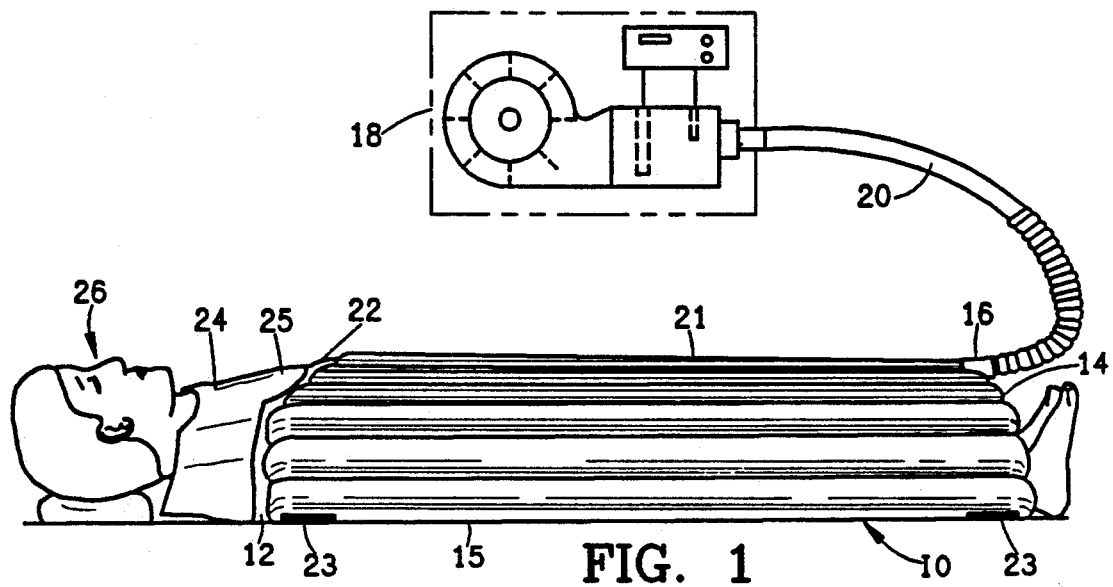
FIG. 1 is a side elevation view of a thermal blanket constructed in accordance with a first aspect of the invention, with the blanket in use, with associated thermal apparatus indicated schematically.

Our invention is illustrated as we intend for it to be used in a first aspect without a foot drape in FIG. 1. In FIG. 1, a self-erecting, inflatable thermal blanket 10 has a head end 12, a foot end 14 and two lateral edges, one indicated by 15. An inflation inlet cuff 16 is connected to a heater/blower assembly 18 which provides a stream of heated air through a connecting hose 20. When the heater/blower 18 is operated, the stream of heated air flows through the inflating hose 20 into the thermal blanket 10 through the inflation cuff 16. When the blanket is inflated, it erects itself into a Quonset hut-like structure with a quilted upper surface 21. As described below, a pattern of apertures on the undersurface of the blanket (not shown in FIG. 1) convectively delivers the inflating heated air into the interior space enclosed by the erected thermal blanket.

The contour of the inflatable portion of the thermal blanket 10 is varied at the head end 12 of the blanket to provide a non-inflated blanket recess 22 in the quilted upper surface 21, which remains smooth and flat when the blanket is inflated and erected. Circulation of the heating air is accelerated through the thermal blanket by exhaust port openings in the upper surface, adjacent the lateral edges of the blanket. Two exhaust ports openings are indicated by reference numeral 23. Further, a bib 24 made of an absorbent material is attached to the head end 12 of the thermal blanket in the vicinity of the non-inflated recess 22. In fact, as shown in FIG. 1, the bib 24 includes a semi-circular tab 25 that extends into the recess 22.

As illustrated in FIG. 1, the thermal blanket of the invention is inflated, erects itself into a bathing structure, and bathes a patient 26 with the thermally-controlled air used to inflate the structure. While the patient is being thermally bathed, the uninflated recess 22 permits observation of the patient's head, face, neck, and chest from almost any location with respect to the thermal blanket 10. Thus, if the patient is placed on a gurney or a bed, the head of which is against a wall, a care giver such as a nurse, intern, resident, or doctor, can keep the patient's face under observation from the foot end 14 of the thermal blanket 20. Respiration can be detected by the rise and fall of the bib and uninflated area, which rest directly on the patient's chest. Moreover, the bib 24 will provide an absorbent sink for stray, unconfined liquids in the area of the patient's head or at the head end 12 of the thermal blanket 10.

Figure 2:
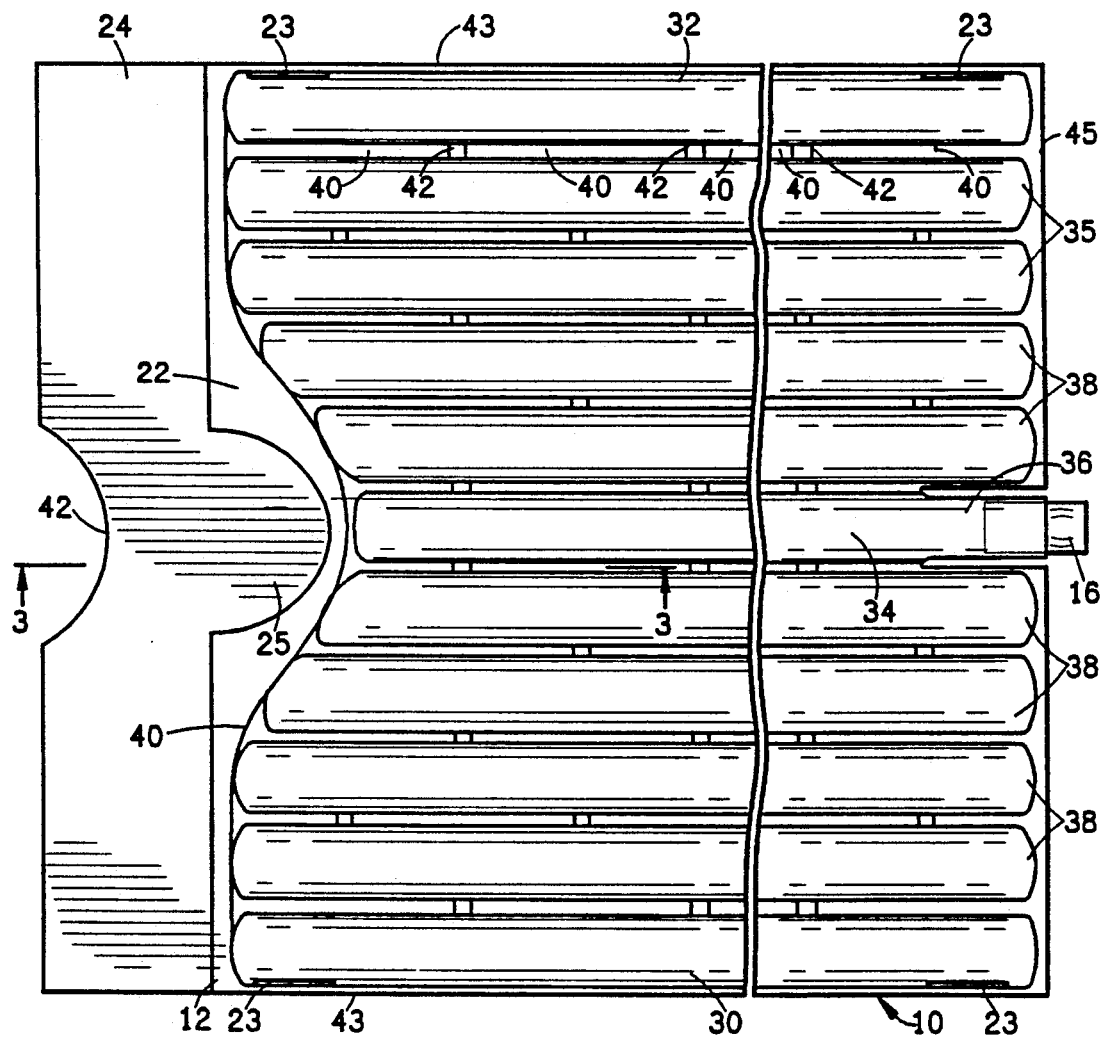
FIG. 2 is an enlarged top plan view of the thermal blanket opened flat.

FIG. 2 is a plan view of the thermal blanket 10 opened flat to show details of its structure. FIG. 2 illustrates the upper surface of the thermal blanket, that is the side that is visible in FIG. 1. As seen, the upper surface consists of a parallel array of elongated tubes, of which 30 and 32 are the lateralmost tubes, 34 is the center tube, and the tubes 38 are arrayed between one of the lateralmost tubes, 34 is the center tube, and the tubes 38 are arrayed between one of the lateralmost tubes and the center tube. Each tube is separated from an adjacent tube by a discontinuous seam, one of which is indicated by 40. The seam 40 separates the tube 32 and its nearest adjacent neighbor 38. The discontinuous seam 40 is interrupted by passageways 42 communicating between the tubes. An interrupted seam separates every tube from one adjacent neighboring tube. The seams permit the thermal blanket, when inflated, to assume a tubular structure on the upper surface, while the ports 42 permit full circulation of the inflating medium throughout the array of tubes. The foot-end seam 45 is continuous. The tubes are inflated through the center tube 34 which transitions to a port 36, through which the inflation cuff 16 is inserted. The edge seams 43 are discontinuous only at the exhaust port opening locations 23. A seal can be made between the inflation port 36 and the inflation cuff 16 by any conventional means, for example, an o-ring, or even tape. When the inflating medium is introduced into the center tube 34, it flows laterally from the center tube into all of the other tubes through the ports 42. Near the head end 12, a continuous seam 40 defines the forward end of all of the tubes, with the seam assuming a bell-curve shape. On the head end side of the seam 40, the thermal blanket 10 is uninflatable. The bell-shaped seam 40 thus defines the uninflatable area 22 at the head end of the thermal blanket 10, which is essentially coplanar with, or substantially parallel to, the underside of the blanket. As shown in FIG. 1, by virtue of its structural integration with the rest of the thermal blanket 10, the non-inflated recess extends over the upper chest of the patient 26 when the blanket is inflated. However, since the recess 22 is uninflated, it provides a wide-angled viewing gap in the inflated contour of the upper surface 21. The gap is filled by continuation of the underside of the blanket. It is also noted that the pattern of inflatable tubes can be replaced by other suitable patterns of communicating, inflatable chambers. The tubes are preferred since they impart strength and shape to the erected bathing structure; other inflatable structures are contemplated, however.

The absorbent bib has an indent 44 cut into its outside edge, which permits the blanket to be drawn up to the chin of a patient and which provides absorbency laterally up the neck of the patient. The absorbent bib can consist of any absorbent material such as a single- or multi-ply tissue paper which is used to make paper towels.

Figure 3:
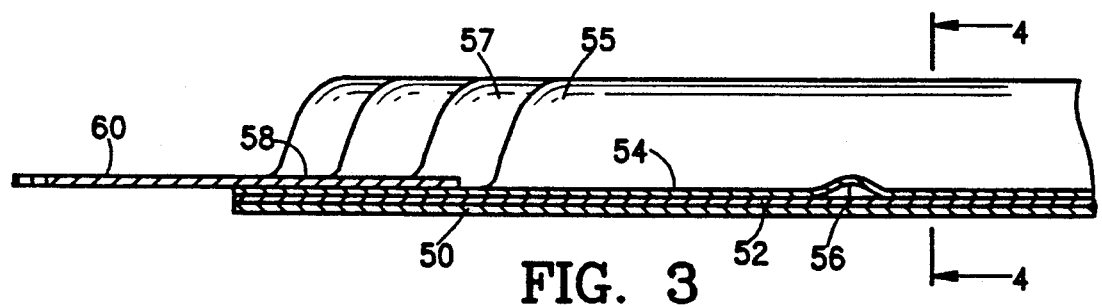
FIG. 3 is an enlarged sectional view taken along 3—3 of FIG. 2.
Figure 4:
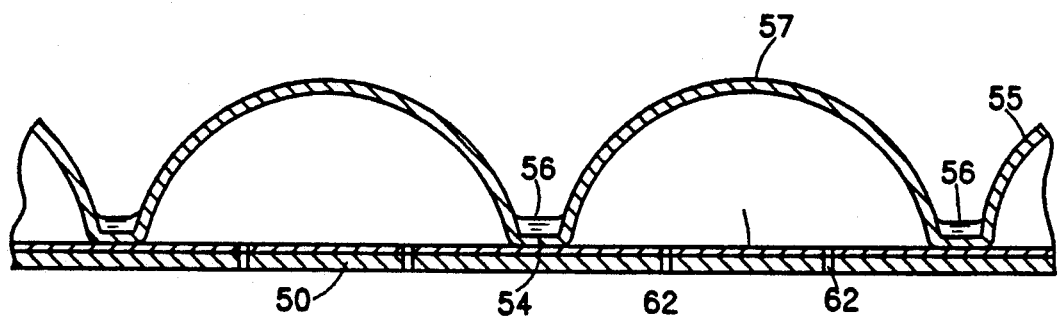
FIG. 4 is a further enlarged sectional view taken along line 4—4 of FIG. 3.

Construction details of the thermal blanket 10 are illustrated in FIGS. 3 and 4. The thermal blanket 10 is assembled from a base sheet consisting of an underside layer 50 formed from flexible material capable of bonding to a layer 52 of heat-sealable plastic. For the layers 50 and 52, we have used a stratum of absorbent tissue paper prelaminated with a layer of heat-sealable plastic. Material of such construction is commercially available in production rolls and is used to make painters' drop cloths. The upper side of the thermal blanket consists of a sheet of plastic bonded to the plastic layer 52 by an interruptible heat-sealing process to form the interrupted seams, one of which is indicated by 54, and the inflatable tubes, one indicated by 55. As can be seen in FIG. 3, the interruption of the seam 54 forms a passageway 56 between adjacent tubes 55 and 57.

The absorbent bib and tab are shown in FIG. 3 as a single material layer 60/58. Alternatively, they may be formed from separate material sheets cut to the outlines illustrated in FIG. 2. The absorbent material forming the bib and tab can be bonded to the upper plastic layer by heat process or by gluing.

The inventors also contemplate deletion of the bib and tab. In this instance, the thermal blanket would still have the viewing recess, which would be defined by the continuous seam at the head end, and which would be filled with the forward portion of the base sheet.

Circulation of heated air through the blanket is enhanced by the exhaust port openings 23, which open through the upper plastic sheet, which is heat sealed to the base of the blanket. The openings 23 vent the heated inflating air out of the outermost tubes 30 and 32, away from the underside of the blanket. Because air can circulate to, and through, the blanket edges, the inflating air in the outermost tubes is hotter than if the openings were absent. This results in hotter air being delivered through the underside apertures toward the edge of the blanket. We have measured the temperature distribution within the thermal blanket for inflating air which is heated to a medium temperature range and for inflating air which is heated to a high temperature range. The results are provided in Table I for a blanket consisting of 13 tubes. Measurements of the temperature of air exhausted through underside apertures were made on the underside of each tube on one side of the blanket. The tubes are numbered 1–6, with 1 being the tube adjacent to the center tube, and tube 6 being the outermost tube adjacent on lateral edge of the blanket. Test apertures were made in the bottom of tube 6 only for the purposes of this test. As is evident, the distribution of temperature within the erected thermal blanket is more uniform when the exhaust port openings are provided. Further, provision of the exhaust ports also increases the average temperature within the erected structure of the blanket. Clearly, the provision of exhaust port openings at the lateral edges of the blanket delivers results which one would not expect when considering the operation of our thermal blanket with no exhaust port openings.

In our first preferred embodiment, the exhaust port openings are slits in the edge seams of our blanket. These slits vary in length from 1¾ to 2 inches. Each edge seam is discontinuous approximately at each corner of the blanket so that inflating air is vented away from the underside of the erected blanket. This keeps the relatively "colder" air at the blanket edges form mixing with the relatively "hotter" air exhausted into the structure through the underside apertures. The result is a "flatter" temperature profile of air within the blanket than without the vents, which raises the average temperature within the erected structure and makes the temperature distribution in the structure more uniform. Resultantly, the clinical effect of the blanket is enhanced. Heating is better controlled, and more uniform, with greater comfort to the patient.

TABLE I

| TUBE NO. | MEDIUM TEMPERATURE RANGE | | HIGH TEMPERATURE RANGE | |
|---|---|---|---|---|
| | WITHOUT EXHAUST PORTS | WITH 2" EXHAUST PORTS | WITHOUT EXHAUST PORTS | WITH 2" EXHAUST PORTS |
| center (inlet) tube | 113.3° F. | 114.1° F. | 121.3° F. | 121.3° F. |
| Tube #1 | 109.9° | 112.3° | 117.3° | 117.7° |
| Tube #2 | 105.3° | 109.8° | 113.4° | 115.0° |
| Tube #3 | 103.2° | 107.1° | 111.0° | 113.3° |
| Tube #4 | 99.9° | 104.3° | 101.4° | 108.6° |
| Tube #5 | 97.2° | 100.0° | 95.7° | 104.4° |
| Tube #6 (outermost) | 85.2° | 95.8° | 89.6° | 99.4° |
| Average temp. under cover | 103.8° | 106.7° | 108.4° | 112.5° |

Figure 5:
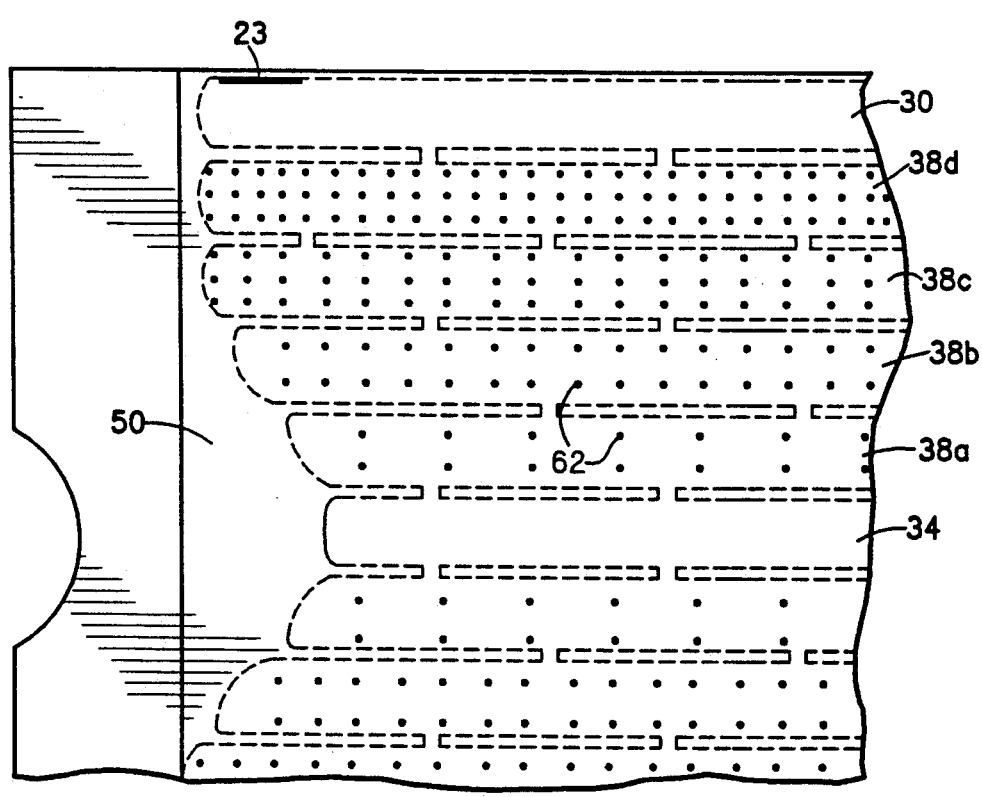
FIG. 5 is a partial underside view of the thermal blanket.

The thermal blanket of the invention is enabled to bathe a patient in the thermally-controlled inflating medium introduced into the upper side tubes by means of a plurality of apertures 62 shown in FIGS. 4 and 5. The apertures extend through the underside of the blanket, which includes the layers 50 and 52. The apertures 62 are made in the footprints of the tubes of the blanket upper side according to a pattern which has been determined to deliver a very uniform thermal bath. In this regard, no apertures are provided through the underside into the lateral most tubes 30 and 32, or into the center tube 34. In addition, the apertures 62 are provided through the underside to the apertured tubes in a density which varies inversely with the proximity of the tube to the center tube 34. Thus, the hole density increases from the tube 38a through the tube 38d. Even with the exhaust port openings, the temperature of the inflating medium exhibits a drop from the center to the lateral most tubes. The varying density of the apertures 62 tends to reduce this gradient further by forcing hotter air to the edges of the blanket. Thus, the thermal bath delivered to the patient is of a generally uniform temperature. The aperture density variation also equalizes the flow of inflating medium out of the apertures. As will be evident, the inflating pressure will be greatest at the center tube 34 and will tend to diminish toward the lateral edges of the thermal blanket. Therefore, fewer apertures are required for the tubes near the center tube 34 to deliver the same amount of air as the relatively greater number of apertures in the tubes at a greater distance from the center tube 34.

The apertures comprise openings which can be of any appropriate shape. For example, we have produced blankets with elongated apertures, approximately ¼ inch in length.

Figure 6:
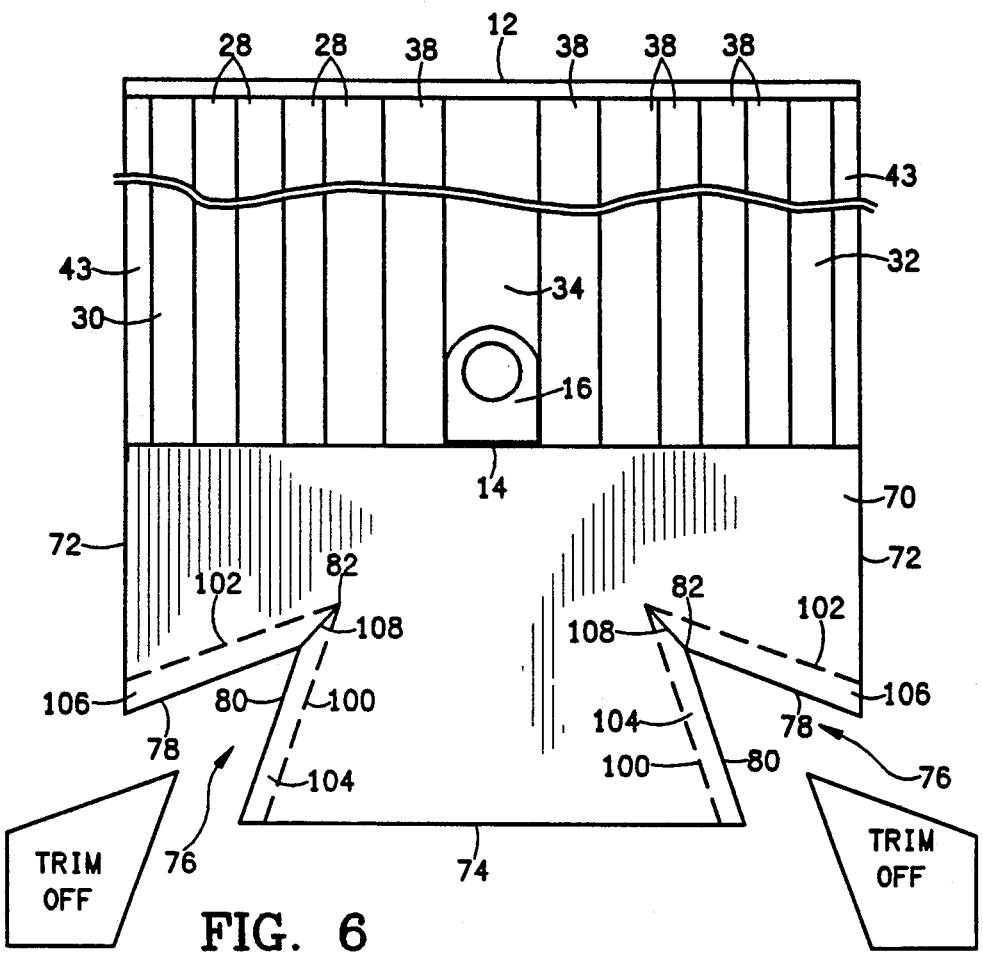
FIG. 6 is a partial diagrammatic top plain view of a thermal blanket constructed in accordance with a second aspect of the invention, with a partially constructed foot drape.
Figure 7:
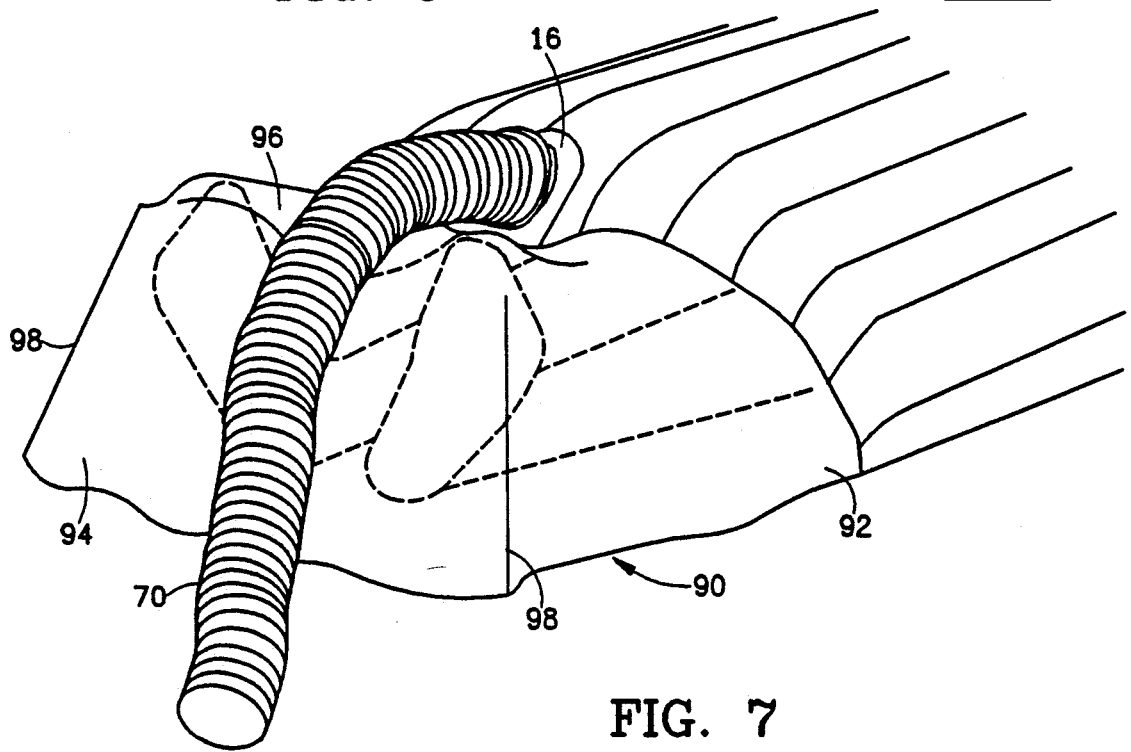
FIG. 7 is a partial projected view of a fully constructed thermal blanket of FIG. 6 in use, with the patient's feet illustrated by hidden lines underlying the foot drape.

Our invention is illustrated as we intend for its to be used in a second aspect including a foot drape in FIG. 7. The foot end 14 of the thermal blanket 10 is modified to provide an uninflated drape forming section 70 formed by a rearward extension of the base sheet 50 beyond the inflatable portion formed by the layer of heat-sealable plastic 52. The drape forming sheet 70 has sides 72 extending parallel to and rearwardly from the outside edge of the edge seams 43, and a rear edge 74. The drape-forming sheet 70 further includes a pair of V-shaped cuts 76 in the rear corners thereof. The V-shaped cuts 76 are formed by converging cuts 78 and 80, extending inwardly from one of the sides 72 and the rear edge 74, respectively, to a point of intersection 82. As shown in FIG. 7, the drape-forming section 70 may be formed into a foot drape 90 that includes a pair of side portions 92, a rear portion 94 and an upper portion 96. The drape 90 is so formed by joining the edges 78 and 80 of the V-shaped cuts 76 to form a pair of seams 98. To form the seams 98, the V-shaped cut edges 78 and 80 may be folded about respective lines 100 and 102 that parallel the edges 78 and 80, as shown in FIG. 6. The resulting respective folded surfaces 104 and 106 may then be fastened together by appropriate means such as heat sealing. Joining the surface 104 and 106 forms a crease 108 and transforms the two dimensional drape forming section 70 into the three dimensional drape 90.

The resulting drape 90 is non-inflatable but erectable under the force of the heated medium circulating around the patient. The drape 90 thus traps and retains heat around the patient's feet to warm the feet. As shown in FIG. 7, the drape 90 also insulates the bare skin of the feet from excessive conductive heat from the inflating hose 70 in the event the hose is oriented in a position wherein it might otherwise come in contact with the feet. Patient warming and comfort is thus further enhanced.

Many modifications and variations of our invention will be evident to those skilled in the art. It is understood that such variations may deviate from specific teachings of this description without departing form the essence of the invention, which is expressed in the following claims.

We claim:

1. A thermal blanket for covering and bathing a person in a thermally-controlled inflating medium, comprising:
   a flexible base sheet having a head end, a foot end, two edges, and a plurality of apertures;
   an overlaying flexible material sheet attached to a first surface of said base sheet by a plurality of discontinuous seams which form said overlaying material sheet into a plurality of communicating, inflatable chambers, said apertures opening through said base sheet into said chambers;
   a continuous seam between said overlaying material sheet and said base sheet at said head end which forms a non-inflatable viewing area in said blanket at said head end, said non-inflatable viewing area being substantially coplanar with, or parallel to said base sheet; and
   a non-inflatable erectable foot drape formed by an extension of the base sheet beyond the foot end of the thermal blanket.

2. The thermal blanket of claim 1 wherein said plurality of apertures in said base sheet are arranged in a pattern wherein the density of apertures increases toward said edges.

3. The thermal blanket of claim 1 further including exhaust ports opening through said overlaying flexible material sheet adjacent said edges for venting the inflating medium from the inflatable chambers and away from said base sheet.

4. The thermal blanket of claim 3 wherein said plurality of apertures in said base sheet is arranged in a pattern wherein the density of apertures between toward said edges.

5. An inflatable thermal blanket for convectively controlling the temperature of a human body, comprising:
   a flexible base sheet having a head end forming a head end of said thermal blanket, a foot end forming a foot end of said thermal blanket, two edges forming respective edges of said thermal blanket, and an undersurface forming an undersurface of said thermal blanket;
   said head end, foot end, and respective edges of the base sheet forming a periphery of said thermal blanket;
   said base sheet including an undersheet of flexible fibrous material and a sheet of plastic material coextensive with and bonded to said undersheet, the undersheet forming said undersurface of the thermal blanket;
   an overlaying, flexible material sheet attached to the plastic material sheet of said base sheet by longitudinal seams to form the base sheet and the overlaying sheet into an inflatable covering which has a plurality of interconnected inflatable chambers;
   an inflating inlet for admitting a thermally controlled, inflating medium into said inflatable chambers to inflate said covering;
   an array of apertures in the base sheet for exhausting a thermally controlled inflating medium from said inflatable chambers through said base sheet in response to inflation and erection of said inflatable covering;
   exhaust ports opening through said overlaying material sheet adjacent said edges for venting the inflating medium from the inflatable chambers and away from the base sheet;
   a continuous seam acting between said overlaying material sheet and said base sheet at said head end to form a non-inflatable viewing extension in said inflatable covering; and
   a non-inflatable foot extension formed in said inflatable covering at said foot end for enclosing and warming a patient's feet in response to inflation of said inflatable covering.

6. The thermal blanket of claim 5 wherein the array of apertures in the base sheet is arranged in a pattern wherein the density of apertures increases toward said edges.

7. The thermal blanket of claim 5 wherein said non-inflatable foot extension comprises a non-inflatable extension of said inflatable covering beyond said foot end.

8. The thermal blanket of claim 7 wherein the non-inflatable foot extension includes an extension of said base sheet.

9. The thermal blanket of claim 5 wherein said longitudinal seams are discontinuous elongate seals formed between said overlaying material sheet and said plastic material sheet.

10. The thermal blanket of claim 9, wherein said discontinuous longitudinal seams form said inflatable covering into said plurality of inflatable chambers, said plurality of inflatable chambers including mutually parallel, communicating tubular chambers.

11. The thermal blanket of claim 9 wherein the non-inflatable foot extension includes an extension of said base sheet beyond said foot end.

12. The thermal blanket of claim 11 wherein the array of apertures in the base sheet is arranged in a pattern wherein the density of apertures increases toward said edges.

13. An inflatable thermal blanket for convectively controlling the temperature of a human body, comprising:
- a flexible base sheet having a head end forming a head end of said thermal blanket, a foot end forming a foot end of said thermal blanket, two edges forming respective edges of said thermal blanket, and an undersurface forming an undersurface of said thermal blanket;
- said head end, foot end, and respective edges of the base sheet forming a periphery of said thermal blanket;
- said base sheet including an undersheet of flexible fibrous material and a sheet of plastic material coextensive with and bonded to said undersheet;
- an overlaying, flexible material sheet attached to the plastic material sheet of said base sheet by longitudinal seams to form the base sheet and the overlaying sheet into an inflatable covering which has a plurality of interconnected inflatable chambers;
- an inflating inlet for admitting a thermally controlled, inflating medium into said inflatable chambers to inflate said covering;
- an array of apertures opening through the base sheet into said chambers for exhausting a thermally controlled inflating medium from said inflatable chambers through said base sheet in response to inflation and erection of said inflatable covering;
- the array of apertures being in a pattern wherein the density of apertures increases toward said edges;
- a continuous seam acting between said overlaying material sheet and said base sheet at said head end to form a non-inflatable viewing extension in said inflatable covering; and
- a non-inflatable foot extension formed in said inflatable covering at said foot end for enclosing and warming a patient's feet in response to inflation of said inflatable covering.

14. The thermal blanket of claim 13, wherein said non-inflatable foot extension comprises a non-inflatable extension of said inflatable covering beyond said foot end.

15. The thermal blanket of claim 13 wherein the non-inflatable foot extension includes an extension of said base sheet beyond said foot end.

16. The thermal blanket of claim 13 wherein said longitudinal seams are discontinuous elongate seals formed between said overlaying material sheet and said sheet of plastic material.

17. The thermal blanket of claim 16 wherein said plurality of discontinuous seams form said overlaying material sheet into said plurality of inflatable chambers, said plurality of inflatable chambers including mutually parallel, communicating tubular chambers.

18. The thermal blanket of claim 17 wherein the non-inflatable foot extension includes an extension of said base sheet beyond said foot end.

* * * * *

UNITED STATES PATENT AND TRADEMARK OFFICE
CERTIFICATE OF CORRECTION

PATENT NO.    :   5,300,102
DATED         :   April 5, 1994
INVENTOR(S)   :   Augustine et al.

It is certified that error appears in the above-indentified patent and that said Letters Patent is hereby corrected as shown below:

Column 8, line 10, please change "between" to --increases--.

Signed and Sealed this

Sixth Day of September, 1994

Attest:

BRUCE LEHMAN

*Attesting Officer*            *Commissioner of Patents and Trademarks*